United States Patent
Krueger et al.

(10) Patent No.: US 7,012,081 B2
(45) Date of Patent: Mar. 14, 2006

(54) ANTHRANYL AMIDES AND THEIR USE AS MEDICAMENTS

(75) Inventors: Martin Krueger, Berlin (DE); Andreas Huth, Berlin (DE); Orlin Petrov, Berlin (DE); Dieter Seidelmann, Berlin (DE); Karl-Heinz Thierauch, Berlin (DE); Martin Haberey, Berlin (DE); Andreas Menrad, Oranienburg (DE); Alexander Ernst, Berlin (DE)

(73) Assignee: Schering AG, Berlin (DE)

( * ) Notice: Subject to any disclaimer, the term of this patent is extended or adjusted under 35 U.S.C. 154(b) by 196 days.

(21) Appl. No.: 10/275,479

(22) PCT Filed: May 7, 2001

(86) PCT No.: PCT/EP01/05168

§ 371 (c)(1),
(2), (4) Date: Jun. 23, 2003

(87) PCT Pub. No.: WO01/85671

PCT Pub. Date: Nov. 15, 2001

(65) Prior Publication Data

US 2004/0029880 A1 Feb. 12, 2004

(30) Foreign Application Priority Data

May 9, 2000 (DE) .......................................... 100 23 484

(51) Int. Cl.
*A61K 31/47* (2006.01)
*C07D 215/00* (2006.01)
*C07D 217/00* (2006.01)

(52) U.S. Cl. ...................... 514/310; 514/313; 514/619; 546/143; 546/159; 564/163

(58) Field of Classification Search ................. 514/310, 514/313, 619; 546/143, 159; 564/163
See application file for complete search history.

(56) References Cited

U.S. PATENT DOCUMENTS 3,226,394 A * 12/1965 Schipper ..................... 546/337

FOREIGN PATENT DOCUMENTS

| WO | WO 9609294 A | | 3/1996 |
| WO | WO 00/27819 | * | 3/2000 |
| WO | WO 0027819 A | | 5/2000 |
| WO | WO 0027820 A | | 5/2000 |
| WO | WO 0039118 A | | 7/2000 |

OTHER PUBLICATIONS

Database Registry (Online) Chemical Abstracts Service, Columbus, Ohio, US.

* cited by examiner

*Primary Examiner*—Zinna Northington Davis
(74) *Attorney, Agent, or Firm*—Miller, White, Zelano, Branigan, P.C.

(57) ABSTRACT

Substituted anthranilamides and use thereof as pharmaceutical agents for treating diseases that are triggered by persistent angiogenesis as well as their intermediate products for the production of anthranilamides are described.

12 Claims, No Drawings

ANTHRANYL AMIDES AND THEIR USE AS MEDICAMENTS

The invention relates to substituted anthranilamides and their use as pharmaceutical agents for treating diseases that are triggered by persistent angiogenesis as well as their intermediate products for the production of anthranilamides.

Persistent angiogenesis can be the cause of various diseases, such as psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases and arteriosclerosis or can result in an aggravation of these diseases.

Direct or indirect inhibition of the VEGF receptor (VEGF=vascular endothelial growth factor) can be used for treating such diseases and other VEGF-induced pathological angiogenesis and vascular permeable conditions, such as tumor vascularization. For example, it is known that the growth of tumors can be inhibited by soluble receptors and antibodies against VEGF.

Persistent angiogenesis is induced by the factor VEGF via its receptor. So that VEGF can exert this action, it is necessary that VEGF bind to the receptor, and a tyrosine phosphorylation is induced.

It has now been found that compounds of general formula I

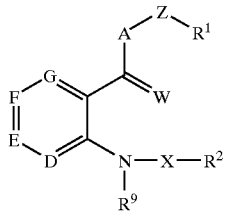

in which

A stands for the group $=NR^7$,

W stands for oxygen, sulfur, two hydrogen atoms or the group $=NR^8$,

Z stands for a bond, the group $=NR^{10}$ or $=N-$, branched or unbranched $C_{1-12}$-alkyl or the group

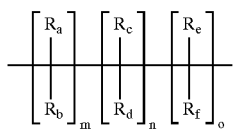

m, n and o stand for 0–3, $R_a$, $R_b$, $R_c$, $R_d$, $R_e$, $R_f$, independently of one another, stand for hydrogen, fluorine, $C_{1-4}$ alkyl or the group $=NR^{11}$, and/or $R_a$ and/or $R_b$ can form a bond with $R_c$ and/or $R_d$, or $R_c$ can form a bond with $R_e$ and/or $R_f$, or up to two of radicals $R_a$–$R_f$ can close a bridge with up to 3 C-atoms each to form $R^1$ or to form $R^7$, $R^1$ stands for branched or unbranched $C_1$–$C_{12}$-alkyl or $C_{2-12}$-alkenyl that is optionally substituted in one or more places with halogen, hydroxy, $C_{1-6}$-alkyloxy, aralkyloxy, $C_{1-6}$-alkyl; and/or $NR^{12}R^{13}$; or $C_{3-10}$-cycloalkyl or $C_{3-10}$-cycloalkenyl that is optionally substituted in one or more places with halogen, hydroxy, $C_{1-6}$alkyloxy, $C_{1-6}$-alkyl and/or $NR^{12}R^{13}$; or aryl or hetaryl that is optionally substituted in one or more places with halogen, hydroxy, $C_{1-6}$-alkyloxy, aralkyloxy, $C_{1-6}$-alkyl and/or $C_{1-6}$-alkyl that is substituted in one or more places with halogen, X stands for $C_{1-6}$-alkyl, $R^2$ stands for $C_{3-10}$ alicyclene, alicyclic ketones or non-aromatic heterocyclic compounds that are unsubstituted or optionally substituted in one or more places with halogen, $C_{1-6}$-alkyl, $C_{1-6}$-alkoxy, $C_{1-6}$-acyl, amino, $C_{1-6}$-carboxyalkylamino and/or hydroxy, and D means N or C—$R^3$, E means N or C—$R^4$, F means N or C—$R^5$, and G means N or C—$R^6$, whereby $R^3$, $R^4$, $R^5$ and $R^6$ stand for hydrogen, halogen or $C_{1-6}$-alkoxy, $C_{1-6}$-alkyl or $C_{1-6}$-carboxyalkyl that is unsubstituted or optionally substituted in one or more places with halogen, $R^7$ stands for hydrogen or $C_{1-6}$-alkyl or forms a bridge with to up 3 ring members with $R_a$–$R_f$ from Z or to form $R^1$, $R^8$, $R^9$, $R^{10}$ and $R^{11}$ stand for hydrogen or $C_{1-6}$-alkyl, $R^{12}$ and $R^{13}$ stand for hydrogen or $C_{1-6}$-alkyl or form a ring that can contain another heteroatom, as well as isomers and salts thereof, stop a tyrosine phosphorylation or persistent angiogenesis and thus prevent the growth and propagation of tumors.

If $R^7$ forms a bridge to $R^1$, heterocyclic compounds are produced, to which $R^1$ is fused. For example, there can be mentioned:

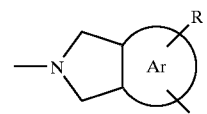

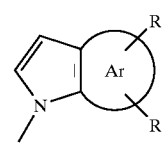

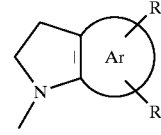

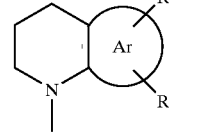

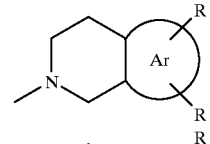

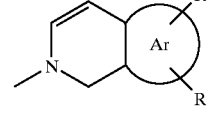

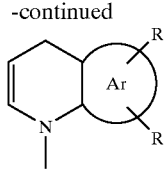

If $R_a$, $R_b$, $R_c$, $R_d$, $R_e$, $R_f$, independently of one another, represent hydrogen or $C_{1-4}$ alkyl, Z forms an alkyl chain.

If $R_a$ and/or $R_b$ form a bond with $R_c$ and/or $R_d$, or $R_c$ and/or $R_d$ form a bond with $R_e$ and/or $R_f$, Z stands for an alkenyl chain or an alkinyl chain.

If $R_a$–$R_f$ form a bridge with themselves, Z represents a cycloalkyl group or a cycloalkenyl group.

If up to two of the radicals $R_a$–$R_f$ form a bridge with up to 3 C atoms to form $R^1$, Z together with $R^1$ is a benzocondensed or a hetaryl-condensed (Ar) cycloalkyl. For example, there can be mentioned:

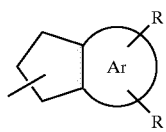
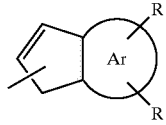
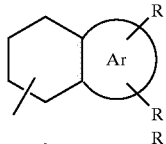
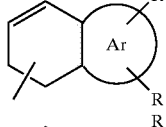
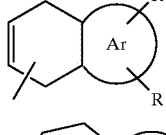
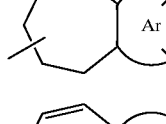
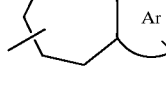

If one of the radicals $R_a$–$R_f$ closes a bridge to form $R^7$, a nitrogen heterocyclic compound is formed, which can be separated from $R^1$ by a group. For example, there can be mentioned:

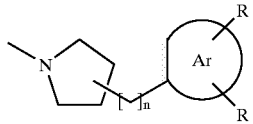
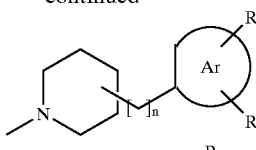
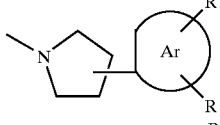
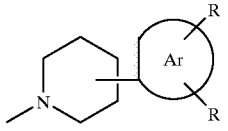
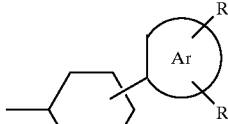
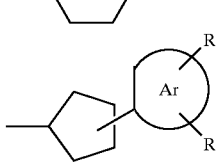

Alkyl is defined in each case as a straight-chain or branched alkyl radical, such as, for example, methyl, ethyl, propyl, isopropyl, butyl, isobutyl, sec-butyl, pentyl, isopentyl or hexyl, heptyl, octyl, nonyl, decyl, undecyl, or dodecyl.

Cycloalkyls are defined as monocyclic alkyl rings, such as cyclopropyl, cyclobutyl, cyclopentyl, cyclohexyl, or cycloheptyl, cyclooctyl, cyclononyl or cyclodecyl, but also bicyclic rings or tricyclic rings, such as, for example, adamantanyl.

Alicyclic ketones are defined as monocyclic ketones such as cyclopropanone, cyclobutanone, cyclopentanone, cyclohexanone, or cycloheptanone as well as oximes thereof, whereby the linkage point is not specified.

Cycloalkenyl is defined in each case as cyclobutenyl, cyclopentenyl, cyclohexenyl, cycloheptenyl, cyclooctenyl, cyclononenyl or cyclodecenyl, whereby the linkage can be carried out both to the double bond and to the single bonds.

The alicyclic alkyl, alkenyl compounds as well as ketones can be substituted in each case in one or more places by halogen, hydroxy, $C_{1-4}$-alkoxy or $C_{1-4}$-alkyl.

Halogen is defined in each case as fluorine, chlorine, bromine or iodine.

The alkenyl substituents are in each case straight-chain or branched and contain 2–6, preferably 2–4, C atoms. For example, the following radicals can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, and allyl.

The aryl radical in each case has 6–12 carbon atoms, such as, for example, naphthyl, biphenyl and especially phenyl.

The heteroaryl radical in each case can be benzocondensed. For example, thiophene, furan, oxazole, thiazole, imidazole, pyrazole and benzo derivatives thereof can be mentioned as 5-ring heteroaromatic compounds, and pyridine, pyrimidine, triazine, quinoline, isoquinoline and benzo derivatives can be mentioned as 6-ring heteroaromatic compounds.

The aryl radical and the heteroaryl radical in each case can be substituted in the same way or differently in 1, 2 or 3 places with hydroxy, halogen, $C_{1-4}$-alkoxy, with $C_{1-4}$-alkyl or $C_{1-4}$-alkyl that is substituted in one or more places with halogen.

Non-aromatic heterocyclic compounds are defined as 4- to 8-membered heterocyclic compounds that contain one or more heteroatoms such as nitrogen, oxygen or sulfur. As 4-rings, for example, there can be mentioned: oxetane and azetidine. As 5-rings, for example, there can be mentioned: tetrahydrofuran, tetrahydrothiophene, pyrroline, pyrrolidine, oxazolidine, and imidazolidine. As 6-rings, for example, there can be mentioned: tetrahydropyran, dihydropyran, tetrahydrothiopyran, piperidine, dihydropyridine, and hexahydropyrimidine. As 7-rings, for example, there can be mentioned: hexahydrooxepine, hexahydroazepine, hexahydrodiazepine, and hexahydrothiepin.

The non-aromatic heterocyclic compounds can be substituted in each case by hydroxy, oxo, halogen, $C_{1-4}$-alkoxy, with $C_{1-4}$-alkyl or $C_{1-4}$-alkyl that is substituted in one or more places with halogen.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, i.a.

Preferred compounds are those compounds of general formula I, in which

A stands for the group $=NR^7$,

W stands for oxygen, sulfur, two hydrogen atoms or the group $=NR^8$,

Z stands for a bond, $R^1$ stands for branched or unbranched $C_1$–$C_{12}$-alkyl or $C_{2-12}$-alkenyl that is optionally substituted in one or more places with halogen, hydroxy, $C_{1-6}$-alkoxy, aralkyloxy, $C_{1-6}$-alkyl and/or $NR^{12}R^{13}$; or $C_{3-10}$-cycloalkyl or $C_{3-10}$-cycloalkenyl that is optionally substituted in one or more places with halogen, hydroxy, $C_{1-6}$-alkyloxy, $C_{1-6}$-alkyl and/or $NR^{12}R^{13}$; or aryl or hetaryl that is optionally substituted in one or more places with halogen, hydroxy, $C_{1-6}$-alkyloxy, aralkyloxy, $C_{1-6}$-alkyl and/or $C_{1-6}$-alkyl that is substituted in one or more places with halogen, X stands for $C_{1-6}$-alkyl, $R^2$ stands for $C_{3-10}$ alicyclene, alicyclic ketones or non-aromatic heterocyclic compounds that are unsubstituted or optionally substituted in one or more places with halogen, $C_{1-6}$-alkyl, $C_{1-6}$-alkoxy, $C_{1-6}$-acyl, amino, $C_{1-6}$-carboxyalkylamino and/or hydroxy, and D means N or C—$R^3$, E means N or C—$R^4$, F means N or C—$R^5$, and G means N or C—$R^6$, whereby $R^3$, $R^4$, $R^5$ and $R^6$ stand for hydrogen, halogen or $C_{1-6}$-alkoxy, $C_{1-6}$-alkyl or $C_{1-6}$-carboxyalkyl that is unsubstituted or optionally substituted in one or more places with halogen, $R^7$ stands for hydrogen or $C_{1-6}$-alkyl, $R^8$ and $R^9$ stand for hydrogen or $C_{1-6}$-alkyl, and $R^{12}$ and $R^{13}$ stand for hydrogen or $C_{1-6}$-alkyl or form a ring that can contain another heteroatom, as well as isomers and salts thereof.

Compounds of general formula I, in which

A stands for the group $=NR^7$,

W stands for oxygen,

Z stands for a bond, $R^1$ stands for branched or unbranched $C_1$–$C_{12}$-alkyl or $C_{2-12}$-alkenyl that is optionally substituted in one or more places with halogen, hydroxy, $C_{1-6}$-alkyloxy, aralkyloxy, $C_{1-6}$-alkyl; and/or $NR^{12}R^{13}$; or $C_{3-10}$-cycloalkyl or $C_{3-10}$-cycloalkenyl that is optionally substituted in one or more places with halogen, hydroxy, $C_{1-6}$-alkyloxy, $C_{1-6}$-alkyl and/or $NR^{12}R^{13}$; or aryl or hetaryl that is optionally substituted in one or more places with halogen, hydroxy, $C_{1-6}$-alkyloxy, aralkyloxy, $C_{1-6}$-alkyl and/or $C_{1-6}$-alkyl that is substituted in one or more places with halogen, X stands for $C_{1-6}$-alkyl, $R^2$ means $C_{3-10}$ alicyclene, alicyclic ketones or non-aromatic heterocyclic compounds that are unsubstituted or optionally substituted in one or more places with halogen, $C_{1-6}$-alkyl, $C_{1-6}$-alkoxy, $C_{1-6}$-acyl, amino, $C_{1-6}$-carboxyalkylamino and/or hydroxy, and D means N or C—$R^3$, E means N or C—$R^4$, F means N or C—$R^5$, and G means N or C—$R^6$, whereby $R^3$, $R^4$, $R^5$ and $R^6$ stand for hydrogen, halogen or $C_{1-6}$-alkoxy, $C_{1-6}$-alkyl or $C_{1-6}$-carboxyalkyl that is unsubstituted or optionally substituted in one or more places with halogen, $R^7$ stands for hydrogen or $C_{1-6}$-alkyl, $R^9$ stands for hydrogen or $C_{1-6}$-alkyl, and $R^{12}$ and $R^{13}$ stand for hydrogen or $C_{1-6}$-alkyl or form a ring that can contain another heteroatom, as well as isomers and salts thereof, have proven quite especially valuable.

Those compounds of general formula I, in which

A stands for the group $=NR^7$,

W stands for oxygen,

Z stands for a bond, $R^1$ stands for branched or unbranched $C_1$–$C_{12}$-alkyl or $C_{2-12}$-alkenyl that is optionally substituted in one or more places with halogen, hydroxy, $C_{1-6}$-alkyloxy, aralkyloxy, $C_{1-6}$-alkyl, and/or $NR^{12}R^{13}$; or $C_{3-10}$-cycloalkyl or $C_{3-10}$-cycloalkenyl that is optionally substituted in one or more places with halogen, hydroxy, $C_{1-6}$-alkyloxy, $C_{1-6}$-alkyl and/or $NR^{12}R^{13}$; or aryl or hetaryl that is optionally substituted in one or more places with halogen, hydroxy, $C_{1-6}$-alkyloxy, aralkyloxy, $C_{1-6}$-alkyl and/or $C_{1-6}$-alkyl that is substituted in one or more places with halogen, X stands for $C_{1-6}$-alkyl, $R^2$ means $C_{3-10}$ alicyclene, alicyclic ketones or non-aromatic heterocyclic compounds that are unsubstituted or optionally substituted in one or more places with halogen, $C_{1-6}$-alkyl, $C_{1-6}$-alkoxy, $C_{1-6}$-acyl, amino, $C_{1-6}$-carboxyalkylamino and/or hydroxy, and D means C—$R^3$, E means C—$R^4$, G means C—$R^6$, whereby $R^3$, $R^4$, $R^5$ and $R^6$ stand for hydrogen, halogen or $C_{1-6}$-alkoxy, $C_{1-6}$-alkyl or $C_{1-6}$-carboxyalkyl that is unsubstituted or optionally substituted in one or more places with halogen, $R^7$ stands for hydrogen or $C_{1-6}$-alkyl, $R^9$ stands for hydrogen or $C_{1-6}$-alkyl, and $R^{12}$ and $R^{13}$ stand for hydrogen or $C_{1-6}$-alkyl or form a ring that can contain another heteroatom, as well as isomers and salts thereof, are also of special interest.

Those compounds of general formula I, in which

A stands for the group $=NR^7$,

W stands for oxygen,

Z stands for a bond, $R^1$ stands for phenyl or isoquinolinyl that is optionally substituted in one or more places with halogen and/or trifluoromethyl, X stands for $C_{1-6}$-alkyl, $R^2$ stands for cyclohexyl, piperidinyl or oxocyclohexyl that is unsubstituted or optionally substituted in one or more places with halogen, $C_{1-6}$-alkyl, $C_{1-6}$-alkoxycarbonyl, $C_{1-6}$-alkylenedioxy or phenyl, and D means C—$R^3$, E means C—$R^4$, F means C—$R^5$, G means C—$R^6$, whereby $R^3$, $R^4$, $R^5$ and $R^6$ stand for hydrogen, and $R^7$ and $R^9$ stand for hydrogen, as well as isomers and salts thereof, are of quite special interest.

The compounds according to the invention prevent a phosphorylation, i.e., certain tyrosine kinases can be inhibited selectively, whereby the persistent angiogenesis can be stopped. Thus, for example, the growth and the propagation of tumors is stopped.

The compounds of general formula I according to the invention also contain the possible tautomeric forms and comprise the E-isomers or Z-isomers, or, if a chiral center is present, also the racemates and enantiomers.

The compounds of formula I as well as their physiologically compatible salts can be used as pharmaceutical agents based on their inhibitory activity relative to the phosphorylation of the VEGF receptor. Based on their profile of action, the compounds according to the invention are suitable for treating diseases that are caused or promoted by persistent angiogenesis.

Since the compounds of formula I are identified as inhibitors of the tyrosine kinases KDR and FLT, they are suitable in particular for treating those diseases that are caused or promoted by persistent angiogenesis that is triggered via the VEGF receptor or by an increase in vascular permeability.

The subject of this invention is also the use of the compounds according to the invention as inhibitors of the tyrosine kinases KDR and FLT.

Subjects of this invention are thus also pharmaceutical agents for treating tumors or use thereof.

The compounds according to the invention can be used either alone or in a formulation as pharmaceutical agents for treating psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis and injuries to nerve tissue.

In treating injuries to nerve tissue, quick scar formation on the injury sites can be prevented with the compounds according to the invention, i.e., scar formation is prevented from occurring before the axons reconnect. A reconstruction of the nerve compounds was thus facilitated.

The formation of ascites in patients can also be suppressed with the compounds according to the invention. VEGF-induced edemas can also be suppressed.

Such pharmaceutical agents, their formulations and uses, are also subjects of this invention.

The invention also relates to the use of the compounds of general formula I for the production of a pharmaceutical agent for treating tumors; psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, and injuries to nerve tissue.

The formation of ascites in patients can also be suppressed with the compounds according to the invention. VEGF-induced edemas can also be suppressed.

To use the compounds of formula I as pharmaceutical agents, the latter are brought into the form of a pharmaceutical preparation, which in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions or emulsions. They also contain, moreover, adjuvants such as preservatives, stabilizers, wetting agents or emulsifiers, salts for changing osmotic pressure or buffers.

For parenteral administration, especially injection solutions or suspensions, especially aqueous solutions of the active compounds in polyhydroxyethoxylated castor oil, are suitable.

As carrier systems, surface-active adjuvants such as salts of bile acids or animal or plant phospholipids, but also mixtures thereof as well as liposomes or components thereof can also be used.

For oral administration, especially tablets, coated tablets or capsules with talc and/or hydrocarbon vehicles or binders, such as for example, lactose, corn starch or potato starch, are suitable. The administration can also be carried out in liquid form, such as, for example, as juice, to which optionally a sweetener or, if necessary, one or more flavoring substances, is added.

The dosage of the active ingredients can vary depending on the method of administration, age and weight of the patient, type and severity of the disease to be treated and similar factors. The daily dose is 0.5–1000 mg, preferably 50–200 mg, whereby the dose can be given as a single dose to be administered once or divided into 2 or more daily doses.

The above-described formulations and forms for dispensing are also subjects of this invention.

The production of the compounds according to the invention is carried out according to methods that are known in the art. For example, compounds of formula I are obtained, in that a) a compound of general formula II

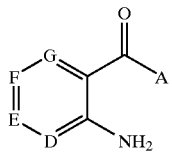
II in which D to G have the above-mentioned meanings, and A is $OR^{13}$, whereby $R^{13}$ is hydrogen or $C_{1-4}$-alkyl or $C_{1-4}$-acyl, is obtained by first having the amine be alkylated and COA then be converted into an amide, or $NH_2$ be converted into halogen, A be converted into an amide, and halogen be converted into the corresponding amine, and optionally a protective group be cleaved, an amine be acylated or a ketone be reduced, whereby the amine is converted into an oxime or converted, by expanding the ring, into an amide or lactone, or b) a compound of formula III

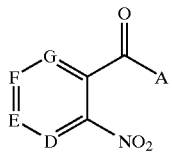
III in which D to G have the above-mentioned meaning, and A is halogen or $OR^{13}$, whereby $R^{13}$ can be hydrogen, low alkyl or acyl, is obtained by having COA be converted into an amide, and the nitro group be reduced to amine and then alkylated, or c) a compound of formula IV

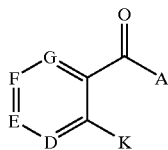
IV in which D to G have the above-mentioned meaning, and K means hydroxy or halogen, and A is halogen or $OR^{13}$, whereby $R^{13}$ can be hydrogen, low alkyl or acyl, is obtained by having K be converted into an amine, COA be converted into an amide, or, if K means hydroxy, by having K be converted into halogen and then having the process be continued as above, or d) a compound of formula V

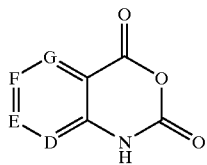
V is obtained by having it first be alkylated, and having the anhydride then be converted into the amide.

The sequence of steps can be reversed in all cases.

The amide formation is carried out according to methods that are known in the literature.

For amide formation, it is possible to start from a corresponding ester. The ester is reacted according to J. Org. Chem. 1995, 8414 with aluminum trimethyl and the corresponding amine in solvents such as toluene at temperatures of 0° C. up to the boiling point of the solvent. If the molecule contains two ester groups, both are converted into the same amide.

When nitrites are used instead of ester, amidines are obtained under analogous conditions.

For amide formation, however, all processes that are known from peptide chemistry are also available. For example, the corresponding acid can be reacted with the amine in aprotic polar solvents, such as, for example, dimethylformamide, via an activated acid derivative, that can be obtained, for example, with hydroxybenzotriazole and a carbodiimide, such as, for example, diisopropylcarbodiimide, or else with preformed reagents, such as, for example, HATU (Chem. Comm. 1994, 201) or BTU, at temperatures of between 0° C. and the boiling point of the solvent. For the amide formation, the process can also be used with the mixed acid anhydride, acid chloride, imidazolide or azide. When acid chloride is reacted, dimethylacetamide is preferred as a solvent at temperatures from room temperature up to the boiling point of the solvent, preferably at 80–100° C.

If various amide groups are to be introduced into the molecule, for example, the second ester group must be introduced into the molecule after the first amide group is produced and then amidated, or one molecule is in one group as an ester while the other is present as acid, and the two groups are amidated in succession according to various methods.

Thioamides can be obtained from anthranilamides by reaction with diphosphadithianes according to Bull Soc. Chim. Belg. 87, 229, 1978 or by reaction with phosphorus pentasulfide in solvents such as pyridine or else quite without solvent at temperatures of 0° C. to 200° C.

The reduction of the nitro group is performed in polar solvents at room temperature or elevated temperature. As catalysts for the reduction, metals such as Raney nickel or noble metal catalysts such as palladium or platinum or else palladium hydroxide optionally on vehicles are suitable. Instead of hydrogen, for example, ammonium formate, cyclohexene or hydrazine can also be used in a known way. Reducing agents such as tin(II) chloride or titanium(III) chloride can also be used as complex metal hydrides optionally in the presence of heavy metal salts. As reducing agents, iron can also be used. The reaction is then performed in the presence of an acid, such as, e.g., acetic acid or ammonium chloride optionally with the addition of a solvent, such as, for example, water, methanol, iron/ammonia, etc. In the case of extended reaction time in this variant, an acylation of the amino group can occur.

If an alkylation of an amino group is desired, the amine can be subjected to a reductive alkylation with aldehydes or ketones, whereby the reaction is carried out in the presence of a reducing agent, such as, for example, sodium cyanoborohydride in a suitable inert solvent, such as, for example, ethanol, at temperatures of 0° C. up to the boiling point of the solvent. If a start is made from a primary amino group, a reaction can be carried out optionally in succession with two different carbonyl compounds, whereby mixed derivatives are obtained [Literature, e.g., Verardo et al. Synthesis (1993), 121; Synthesis (1991), 447; Kawaguchi, Synthesis (1985), 701; Micovic et al. Synthesis (1991), 1043]. It may be advantageous first to form the Schiff base by reaction of the aldehyde with the amine in solvents such as ethanol or methanol, optionally with the addition of adjuvants such as glacial acetic acid and then to add only reducing agent, such as, e.g., sodium cyanoborohydride.

An alkylation can also be achieved in that a reaction is carried out according to the Mitsonubo variant with an alcohol in the presence of, for example, triphenylphosphine and azodicarboxylic acid ester. An alkylation of the amino group can also be carried out, however, by alkylating agents such as halides, tosylates, mesylates or triflates. As solvents, for example, polar solvents such as ethanol, tetrahydrofuran, acetonitrile or dimethylformamide are suitable. The addition of an auxiliary base such as triethylamine, DABCO pyridine or potassium carbonate may be advantageous.

Since the risk of double alkylation exists in a free amino group, isatoic acid anhydride can advantageously be used. With bases such as sodium hydride, but also cesium carbonate in solvents such as tetrahydrofuran or dimethylformamide at temperatures of between room temperature and the boiling point of the solvent, preferably at 60° C., it can be converted into the anion that then is further reacted with the alkylating agent.

Ether cleavages are performed according to processes that are common in the literature. In this case, a selective cleavage can also be achieved in several groups that are present in the molecule. In this case, the ether is treated, for example, with boron tribromide in solvents such as dichloromethane at temperatures of between –100° C. up to the boiling point of the solvent, preferably at –78° C. It is also possible, however, to cleave the ether by sodium thiomethylate in solvents such as dimethylformamide. The temperature can be between room temperature and the boiling point of the solvent, preferably at 150° C. In benzyl ethers, the cleavage can also be accomplished with strong acids, such as, for example, trifluoroacetic acid, at temperatures from room temperature up to the boiling point.

The conversion of a hydroxy group, which is in ortho- or para-position to a nitrogen of a 6-ring hetaryl, in halogen, can be performed, for example, by reaction with inorganic acid halides, such as, for example, phosphorus oxychloride, optionally in an inert solvent, at temperatures up to the boiling point of the solvent or the acid halide.

The substitution of a halogen, tosylate, triflate or nonaflate, which is in ortho- or para-position to a nitrogen in a 6-membered heteroaromatic compound, can be accomplished by reaction with a corresponding amine in inert solvents, such as, for example, xylene, or in polar solvents such as N-methylpyrrolidone or dimethylacetamide at temperatures of 60–170° C. Heating without solvent is also possible, however. The addition of an auxiliary base such as potassium carbonate or cesium carbonate, or the addition of copper and/or copper oxide can be advantageous. In the case of non-activated halogens or triflates, a palladium-catalyzed introduction of the amine portion is possible according to J. Org. Chem. 2000, 1158. As a base, preferably sodium-t-butylate is used; as an auxiliary ligand, a biphenylphosphine is used.

The introduction of the halogens chlorine, bromine or iodine via an amino group can be carried out, for example, also according to Sandmeyer, by the diazonium salts that are intermediately formed with nitrites being reacted with copper(I) chloride or copper(I) bromide in the presence of the corresponding acid such as hydrochloric acid or hydrobromic acid or with potassium iodide.

If an organic nitrite is used, the halogens can be introduced, e.g., by adding methylene iodide or tetrabromomethane, into a solvent, such as, for example, dimethylformamide. The removal of the amino group can be achieved either by reaction with an organic nitrite in tetrahydrofuran or by diazotization and reductive boiling-down of the diazonium salt, for example, with phosphorus acid, optionally with the addition of copper(I) oxide.

Introduction of fluorine can be accomplished by, for example, Balz-Schiemann reaction of diazonium tetrafluoroborate or according to J. Fluor. Chem. 76, 1996, 59–62 by diazotization in the presence of HFxpyridine and subsequent boiling-down optionally in the presence of a fluoride ion source, such as, e.g., tetrabutylammonium fluoride.

The cleavage of the ketal protective groups is carried out in a known way, for example, by the reaction being performed in a solvent, such as ethanol or acetone, with an aqueous acid, preferably 4N hydrochloric acid, at temperatures of between room temperature and the boiling point of the solvent.

The cleavage of the t-butoxycarbonyl group is carried out, as is generally known, in that the reaction is performed in a solvent, such as tetrahydrofuran, dioxane or ethanol, with an acid, such as, e.g., 1N hydrochloric acid, at temperatures of between room temperature and the boiling point of the solvent. It is also possible to cleave the t-BOC group with strong acids such as trifluoroacetic acid at temperatures of between –20° C. up to the boiling point, preferably at room temperature. A solvent such as methylene chloride is not absolutely necessary, but it may be advantageous.

The reduction of a ketone takes place in a known way by a complex metal hydride, such as, for example, sodium borohydride or lithium borohydride, in solvents such as ethanol, tetrahydrofuran or diethyl ether, at temperatures of 0° C. up to the boiling point of the solvent.

The acylation of an amine is carried out in a known way either according to the process that is described under amide formation or by reaction with activated acid derivatives, such as, for example, acid chloride or acid anhydride in solvents such as methylene chloride, acetonitrile or tetrahydrofuran, optionally in the presence of bases such as triethylamine. An addition of catalytic amounts of dimethylaminopyridine may be advantageous.

Expanding the ring of a ketone to the next-highest lactone can be achieved by Bayer-Villiger oxidation, for which a number of variants are described. The ketone can be reacted, for example, with a peracid, such as, m-chloroperbenzoic acid or magnesium monoperoxyphthalate in solvents, such as, for example, methylene chloride. A reaction with hydrogen peroxide in formic acid or sodium perborate in trifluoroacetic acid is also possible, however.

Expanding the ring of the ketone to the next-highest lactam can be carried out in a known way by a Schmidt reaction of the ketone or by the Beckmann rearrangement of the oxime. For both reactions, an entire series of variations is described. In the Schmidt reaction, the ketone is reacted, for example, with sodium azide in strong acids, such as concentrated hydrochloric acid, sulfuric acid, trifluoroacetic acid or methanesulfonic acid without solvent or in solvents such as acetonitrile, chloroform or methylene chloride.

In the Beckmann rearrangement, the oxime of a carbonyl compound is reacted with acids such as polyphosphoric acid or trimethylsilyl esters thereof or with Lewis acids, such as aluminum triiodide or iron(III) chloride-impregnated montmorillonite without solvent or in solvents such as acetonitrile at elevated temperature. Mesylate or tosylate of the oxime can also be produced, however, and then treated with bases, such as aqueous sodium hydroxide solution, or with Lewis acids, such as diethylaluminum chloride.

The oxime formation is carried out in a known way by reaction with hydroxylamine hydrochloride in solvents such as ethanol, optionally with the addition of bases, such as pyridine, sodium acetate or aqueous sodium hydroxide solution, at temperatures up to the boiling point of the solvent.

The isomer mixtures can be separated into enantiomers or E/Z isomers according to commonly used methods, such as, for example, crystallization, any form of chromatography or salt formation.

The production of salts is carried out in the usual way, by a solution of the compound of formula I being mixed with the equivalent amount or an excess of a base or acid, which optionally is in solution, and the precipitate being separated or the solution being worked up in the usual way.

The following examples explain the production of the compounds according to the invention, without limiting the scope of the claimed compounds to these examples.

EXAMPLE 1

N-(Isoquinolin-3-yl)-2-(4,4-ethylenedioxy) cyclohexylmethyl)aminobenzoic acid amide 144 mg (1 mmol) of 3-aminoisoquinoline is mixed in 10 ml of absolute toluene under argon and in a moisture-free environment at 4° C. with 0.5 ml of a 2 molar solution of trimethylaluminum in toluene, and it is stirred for 15 minutes at this temperature.

Then, 240 mg (0.92 mmol) of 2-(4,4-ethylenedioxy) cyclohexylmethyl)-aminobenzoic acid methyl ester is added to it, and it is heated for 2 hours to a bath temperature of 120° C. The batch is mixed with 30 ml of a dilute sodium bicarbonate solution and shaken out three times with about 30 ml of ethyl acetate. The combined organic phase is washed with water, dried, filtered and concentrated by evaporation. The residue is chromatographed on silica gel with hexane:ethyl acetate=1:1 as an eluant. 151 mg (39.3% of theory) of 2-(4,4-N-(isoquinolin-3-yl)-2-(4,4-ethylenedioxy)cyclohexylmethyl)aminobenzoic acid amide with a melting point of 176.7° C. is obtained.

Produced in a way similar to Example 1 are:

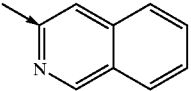

| Example No. | $R^1$ | $R^2$ | $R^6$ | D | Melting Point ° C. |
|---|---|---|---|---|---|
| 1.1 | 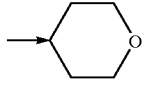 | 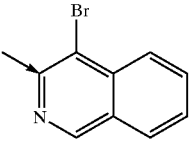 | H | CH | 140.4 |
| 1.2 |  | 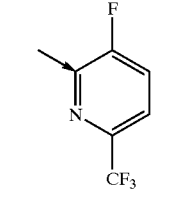 | H | CH | 195.3 |
| 1.3 | 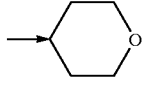 | 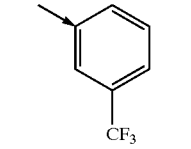 | H | CH | 83.6 |
| 1.4 | 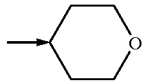 | 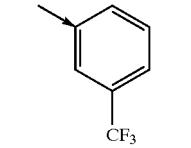 | H | CH | 142.2 |
| 1.5 | 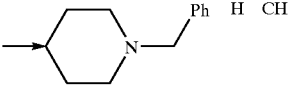 | 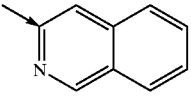 | H | CH | 147.3 |
| 1.6 | 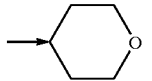 | | F | CH | <180 decomposition |

-continued

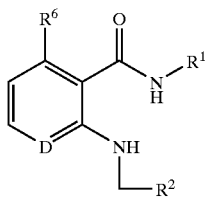

| Example No. | R¹ | R² | R⁶ | D | Melting Point ° C. |
|---|---|---|---|---|---|
| 1.7 | isoquinolin-3-yl (methyl-linked) | cyclohexyl | H | CH | |
| 1.8 | isoquinolin-3-yl (methyl-linked) | N-BOC-piperidin-4-yl | H | CH | |

BOC = tert.-Butoxycarbonyl

EXAMPLE 2

2-(4,4-N-(Isoquinolin-3-yl)-2-(4-oxocyclohexylmethyl)aminobenzoic acid amide 100 mg (0.24 mmol) of 2-(4,4-N-(isoquinolin-3-yl)-2-(4,4-ethylenedioxy)cyclohexylmethyl)-aminobenzoic acid amide is introduced into 15 ml of acetone and mixed with 1 ml of 4N hydrochloric acid. It is stirred for 3 hours at room temperature. Then, the precipitate is suctioned off. The residue is taken up in ethyl acetate and shaken out with 1N sodium hydroxide solution. The insoluble residue is suctioned off. The ethyl acetate phase is dried, filtered and concentrated by evaporation. 66 mg (73% of theory) of 2-(4,4-N-(isoquinolin-3-yl)-2-(4-oxocyclohexylmethyl)aminobenzoic acid amide with a melting point of 147.7° C. is obtained from the residue that is suctioned off and the evaporation residue of the ethyl acetate phase.

EXAMPLE 3

N-(Indazol-5-yl)-2-(tetrahydropyran-4-yl)methylaminobenzoic acid amide 235 mg (1 mmol) of 2-(tetrahydropyran-4-yl)methylaminobenzoic acid is mixed in 10 ml of dimethylformamide with 266 mg (2 mmol) of 5-aminoindazole. 253 mg (2.5 mmol) of N-methylmorpholine and 456 mg (1.2 mmol) of O-(7-azabenzotriazol-1-yl)-1,1,3,3-tetramethyluronium hexafluorophosphate are added to this solution under argon and in a moisture-free environment. This mixture is stirred for 3 hours at room temperature. It is concentrated by evaporation in a vacuum, taken up in dilute sodium bicarbonate solution and extracted three times with 30 ml of ethyl acetate each. The combined organic phase is washed with water, dried, filtered and concentrated by evaporation. The residue is absorptively precipitated in ethyl acetate and suctioned off. The filtrate is concentrated by evaporation, and the residue is chromatographed on silica gel with methylene chloride:ethanol=10:1 as an eluant. 124 mg (35% of theory) of N-(indazol-5-yl)-2-(tetrahydropyran-4-yl)methylaminobenzoic acid amide with a melting point of 173.6° C. is obtained.

EXAMPLE 4

N-Trifluoromethyl 2-(cyclohexylmethylamino)benzoic acid amide 259 mg (1 mmol) of cyclohexylmethylaminonicotinic acid ethyl ester is mixed in 5 ml of N-methylpyrrolidone with 161 mg (1 mmol) of 3-trifluoromethylaniline, and it is heated for 3 hours to a bath temperature of 150° C. The solvent is then drawn off in a vacuum, and the residue is chromatographed on silica gel with cyclohexane:ethyl acetate=1:1 as an eluant. 100 mg of N-trifluoromethyl 2-(cyclohexylmethylamino)benzoic acid amide is obtained.

The following examples explain the production of intermediate products that preferably can be used for the production of the compounds according to the invention.

Production of Intermediate Products

Ethyl-4,4-(ethylenedioxy)cyclohexanecarboxylate is produced according to J. Org. Chem., 62, 5288, 1997.

A. 4,4-(Ethylenedioxy)cyclohexane carbaldehyde 214 mg (1 mmol) of ethyl-4,4-(ethylenedioxy)cyclohexanecarboxylate is cooled in 15 ml of toluene under argon and in a moisture-free environment to −78° C., and it is mixed drop by drop with 0.85 ml of a 1.2 molar solution of diisobutyl aluminum hydride (DIBAH) in toluene. After 15 minutes of stirring at this temperature, it is mixed with about 10 ml of a saturated ammonium chloride solution. The organic phase is separated, washed with saturated common salt solution, dried, filtered and concentrated by evaporation. 148 mg (85% of theory) of 4,4-(ethylenedioxy)cyclohexane carbaldehyde is obtained.

Similarly produced are:
Tetrahydropyranyl-4-carbaldehyde
N-Benzylpiperidine-4-carbaldehyde
N-BOC-4-formylpiperidine
(Produced according to Org. Prep. Proc. Int. 32, 96, 2000)

B. 2-(4,4-Ethylenedioxy)cyclohexylmethyl)aminobenzoic acid methyl Ester 334 mg (2.21 mmol) of anthranilic acid methyl ester is dissolved in 18.4 ml of absolute methanol and mixed with 600 mg (3.53 mmol) of 4,4-(ethylenedioxy)-cyclohexanecarbaldehyde as well as 0.18 ml of glacial acetic acid. The batch is stirred for 24 hours at room temperature, mixed with 22 mg (3.53 mmol) of sodium cyanoborohydride and stirred repeatedly for 24 hours at room temperature. It is then mixed with dilute sodium bicarbonate solution and shaken out three times with 30 ml each of ethyl acetate. The combined organic phase is washed with water, dried, filtered and concentrated by evaporation. The residue is chromatographed on silica gel with hexane:ethyl acetate=8:2 as an eluant. 251 mg (27.2% of theory) of 2-(4,4-ethylenedioxy)cyclohexylmethyl)aminobenzoic acid methyl ester is obtained.

Similarly produced are:

6-Fluoro-2-(tetrahydropyran-4-yl)methylaminobenzoic acid methyl ester 2-(Tetrahydropyran-4-yl)methylaminobenzoic acid methyl ester 2-(1-Benzylpiperidin-4-yl)methylaminobenzoic acid methyl ester C. N-Benzylpiperidine-4-carboxylic acid ethyl ester 1 g (6.4 mmol) of piperidine-4-carboxylic acid ethyl ester is mixed in 10 ml of absolute ethanol with 0.75 ml (6.4 mmol) of benzyl chloride and 1.52 g (11 mmol) of potassium carbonate. The batch is stirred for 30 hours at room temperature. It is then dispersed in ethyl acetate/water. The combined organic phase is washed with water, dried, filtered and concentrated by evaporation. The residue is chromatographed on silica gel with hexane:ethyl acetate=1:1 as an eluant. 991 mg (64% of theory) of N-benzylpiperidine-4-carboxylic acid ethyl ester is obtained.

D. 2-Cyclohexylmethylaminonicotinic acid ethyl ester 391 mg (2 mmol) of 2-carboxyethyliminoacetic acid ethyl ester hydrochloride (produced according to Het. 1996, 43 (9), 1981) is mixed in 5 ml of ethanol with 226 mg (2 mmol) of cyclohexylmethylamine. After 10 minutes, cloudiness sets in. Then, 0.48 ml (2 mmol) of malonic aldehyde diethyl acetal is added, and the batch is refluxed for 4 hours. The batch is concentrated by evaporation. The residue is chromatographed on silica gel with hexane:ethyl acetate=1:1 as an eluant. 150 mg of 2-cyclohexylmethylaminonicotinic acid ethyl ester is obtained.

E. N-Cyclohexylmethylisatoic acid anhydride 815 mg (5 mmol) of isatoic acid anhydride is dissolved in 15 ml of N,N-dimethylacetamide and mixed under cover gas and in a moisture-free environment with 220 mg (5.5 mmol) of sodium hydride (60% dispersion in mineral oil). It is heated for 1 hour to 60° C. After cooling, 885 mg (5 mmol) of cyclohexylmethyl bromide is added, and the batch is heated to 60° C. for 4 hours. It is then diluted with water to 60 ml and shaken out three times with ethyl acetate. The combined organic phase is washed with water, dried, filtered and concentrated by evaporation. The residue is chromatographed on silica gel with hexane:ethyl acetate=1:1 as an eluant. 300 mg of N-cyclohexylmethylisatoic acid anhydride is obtained.

If the production of the intermediate compounds is not described, the latter are known or can be produced analogously to known compounds or to processes that are described here.

The described intermediate compounds are especially suitable for the production of the anthranilamides according to the invention.

The intermediate compounds are thus also subjects of this invention.

The intermediate compounds are themselves partially active and thus can also be used for the production of a pharmaceutical agent for treating tumors; psoriasis; arthritis, such as rheumatoid arthritis, hemangioma, angiofibroma; eye diseases, such as diabetic retinopathy, neovascular glaucoma; renal diseases, such as glomerulonephritis, diabetic nephropathy, malignant nephrosclerosis, thrombic microangiopathic syndrome, transplant rejections and glomerulopathy; fibrotic diseases, such as cirrhosis of the liver, mesangial cell proliferative diseases, arteriosclerosis, and injuries to nerve tissue.

The formation of ascites in patients can also be suppressed with the intermediate compounds according to the invention. VEGF-induced edemas can also be suppressed.

The sample applications below explain the biological action and the use of the compounds according to the invention without the latter being limited to the examples.

Solutions Required for the Tests

Stock Solutions

Stock solution A: 3 mmol of ATP in water, pH 7.0 (−70° C.)

Stock solution B: g-33P-ATP 1 mCi/100 μl

Stock solution C: poly-(Glu4 Tyr) 10 mg/ml in water

Solution for Dilutions

Substrate solvent: 10 mmol of DTT, 10 mmol of manganese chloride, 100 mmol of magnesium chloride Enzyme solution: 120 mmol of tris/HCl, pH 7.5, 10 μM of sodium vanadium oxide Sample Application 1

Inhibition of the KDR- and FLT-1 Kinase Activity in the Presence of the Compounds According to the Invention In a microtiter plate (without protein binding) that tapers to a point, 10 μl of substrate mix (10 μl of volume of ATP stock solution A+25 μCi of g-33P-ATP (about 2.5 μl of stock solution B)+30 μl of poly-(Glu4Tyr) stock solution C+1.21 ml of substrate solvent), 10 μl of inhibitor solution (substances corresponding to the dilutions, 3% DMSO in substrate solvent as a control) and 10 μl of enzyme solution (11.25 μg of enzyme stock solution (KDR or FLT-1 kinase) are added at 4° C. in 1.25 ml of enzyme solution (dilute). It is thoroughly mixed and incubated for 10 minutes at room temperature. Then, 10 μl of stop solution (250 mmol of EDTA, pH 7.0) is added, mixed, and 10 μl of the solution is transferred to a P 81 phosphocellulose filter. Then, it is washed several times in 0.1 M phosphoric acid. The filter paper is dried, coated with Meltilex and measured in a microbeta counter.

The IC50 values are determined from the inhibitor concentration that is necessary to inhibit the phosphate incorporation to 50% of the uninhibited incorporation after removal of the blank reading (EDTA-stopped reaction).

The results of the kinase inhibition IC50 in μM are presented in the table below:

| Example No. | VEGFR I (FLT) | VEGFR II (KDR) |
|---|---|---|
| 1.1 |  | 0.05 |
| 2.0 |  | 0.02 |

KH = No inhibition

What is claimed is:

1. A compound of formula I

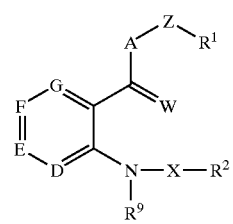

in which

A stands for the group —N($R^7$)—,

W stands for oxygen, or sulfur,

Z stands for a bond, $R^1$ stands for $C_{3-10}$-cycloalkyl or $C_{3-10}$-cycloalkenyl that is optionally substituted in one or more places with halogen, hydroxy, $C_{1-6}$-alkyloxy, $C_{1-6}$-alkyl and/or $NR^{12}R^{13}$; or aryl or hetaryl that is optionally substituted in one or more places with halogen, hydroxy, $C_{1-6}$-alkyloxy, aralkyloxy, $C_{1-6}$-alkyl and/or $C_{1-6}$-alkyl that is substituted in one or more places with halogen, X stands for $C_{1-6}$-alkyl, $R^2$ stands for a $C_{3-10}$ cycloalkyl, cycloalkene, alicyclic or non-aromatic heterocyclic group that is unsubstituted or optionally substituted in one or more places with halogen, $C_{1-6}$-alkyl, $C_{1-6}$-alkoxy, $C_{1-6}$-acyl, amino, $C_{1-6}$-carboxyalkylamino and/or hydroxy, and D means C—$R^3$, E means C—$R^4$, F means C—$R^5$, and G means C—$R^6$, whereby $R^3$, $R^4$, $R^5$ and $R^6$ stand for hydrogen, halogen or $C_{1-6}$-alkoxy, $C_{1-6}$-alkyl or $C_{1-6}$-carboxyalkyl that is unsubstituted or optionally substituted in one or more places with halogen, $R^7$ stands for hydrogen or $C_{1-6}$-alkyl, $R^9$ stands for hydrogen or $C_{1-6}$alkyl, $R^{12}$ and $R^{13}$ stand for hydrogen or $C_{1-6}$-alkyl or together form a ring that can contain another heteroatom, or a pharmaceutically acceptable isomers or salts thereof.

2. A compounds of formula I, according to claim 1, in which

W stands for oxygen, or a pharmaceutically acceptable isomers or salts thereof.

3. A compounds of formula I, according to claim 1, in which $R^1$ stands for phenyl or isoquinolinyl that is optionally substituted in one or more places with halogen and/or trifluoromethyl, $R^2$ stands for cyclohexyl, piperidinyl or oxocyclohexyl that is unsubstituted or optionally substituted in one or more places with halogen, $C_{1-6}$-alkyl, $C_{1-6}$-alkoxycarbonyl, $C_{1-6}$-alkylenedioxy or phenyl, $R^3$, $R^4$, $R^5$ and $R^6$ stand for hydrogen, and $R^7$ and $R^9$ stand for hydrogen, or a pharmaceutically acceptable isomers or salts thereof.

4. A compound of formula I according to claim 1, in which aryl, in each case, is naphthyl, biphenyl or phenyl; and hetaryl, in each case, is thiophene, furan, oxazole, thiazole, imidazole, pyrazole, pyridine, pyrimidine, triazine, quinoline, or isoquinoline, or such rings with a further benzo-condensed ring; each of these rings being optionally substituted in 1, 2 or 3 places with hydroxy, halogen, $C_{1-4}$-alkoxy, $C_{1-4}$-alkyl or $C_{1-4}$-alkyl that is substituted in one or more places with halogen.

5. A compound of formula I, according to claim 1, in which:

the alicyclic ketone group is, in each case, cyclopropanone, cyclobutanone, cyclopentanone, cyclohexanone, or cycloheptanone, or an oxime thereof, each being optionally substituted by halogen, hydroxy, $C_{1-4}$-alkoxy or $C_{1-4}$-alkyl, and the non-aromatic heterocyclic group, in each case, is oxetane, azetidine, tetrahydrofuran, tetrahydrothiophene, pyrroline, pyrrolidine, oxazolidine, imidazolidine, tetrahydropyran, dihydropyran, tetrahydrothiopyran, piperidine, dihydropyridine, hexahydropyrimidine, hexahydrooxepine, hexahydroazepine, hexahydrodiazepine, and hexahydrothiepin, each being optionally substituted by hydroxy, oxo, halogen, $C_{1-4}$-alkoxy, with $C_{1-4}$-alkyl or $C_{1-4}$-alkyl that is substituted in one or more places with halogen.

6. A method for producing a pharmaceutical agent for treating tumors which comprises bringing a compound of the formula I of claim 1, or a pharmaceutically acceptable isomer or salt thereof, together with a suitable formulation substance or vehicle to form a pharmaceutical agent.

7. A pharmaceutical agent that contains at least one compound according to claim 1 and a pharmaceutically acceptable carrier.

8. A pharmaceutical agent according to claim 7 for treating tumors.

9. A pharmaceutical agent according to claim 7 in a form for enteral, parenteral and oral administration.

10. A method for treating tumors in a patient, which comprises administering to the patient an effective amount of a compound of formula I according to claim 1, or a pharmaceutically acceptable isomer or salt thereof.

11. The method of claim 10, wherein the compound of formula I is administered in a daily dose of 0.5–1000 mg.

12. The method of claim 10, wherein the compound of formula I is administered in a daily dose of 50–200 mg.

* * * * *

UNITED STATES PATENT AND TRADEMARK OFFICE
CERTIFICATE OF CORRECTION

PATENT NO. : 7,012,081 B2  Page 1 of 1
APPLICATION NO. : 10/275479
DATED : March 14, 2006
INVENTOR(S) : Martin Krueger et al.

It is certified that error appears in the above-identified patent and that said Letters Patent is hereby corrected as shown below:

Column 19, line 6, reads "alicyclic or" should read -- alicyclic ketone or --
Column 19, line 22, reads "$C_{1-6}$alkyl" should read -- $C_{1-6}$-alkyl --
Column 19, line 25, reads "isomers or salts" should read -- isomer or salt --
Column 19, line 29, reads "isomers or salts" should read -- isomer or salt --
Column 19, line 42, reads "isomers or salts" should read -- isomer or salt --

Signed and Sealed this

Sixth Day of February, 2007

JON W. DUDAS
*Director of the United States Patent and Trademark Office*